United States Patent [19]

O'Leary

[11] Patent Number: 5,593,400
[45] Date of Patent: Jan. 14, 1997

[54] DISPOSABLE ABSORBENT ARTICLE WITH SUSPENDED ABSORBENT STRUCTURE

[75] Inventor: Audrey A. O'Leary, Belfair, Wash.

[73] Assignee: Paragon Trade Brands, Norcross, Ga.

[21] Appl. No.: 193,737

[22] Filed: Feb. 9, 1994

[51] Int. Cl.⁶ .................................................. A61F 13/15
[52] U.S. Cl. .................. 604/385.2; 604/394; 604/396; 604/397; 604/400; 604/401; 604/402; 604/386
[58] Field of Search ............................ 604/385.1–402; 2/400–408, 78.1–78.4; 602/68–73

[56] References Cited

U.S. PATENT DOCUMENTS

| | | | |
|---|---|---|---|
| 501,563 | 7/1893 | Gaines | 604/401 |
| 929,166 | 7/1909 | Plamondon | 604/397 |
| 1,064,298 | 3/1928 | Katz . | |
| 1,768,789 | 7/1930 | Reich | 604/401 |
| 1,919,124 | 7/1933 | Panullo | 604/401 |
| 2,675,806 | 4/1954 | Bram | 604/397 |
| 2,859,752 | 11/1958 | Haber . | |
| 2,881,761 | 4/1959 | Kennor | 604/401 |
| 3,094,990 | 6/1963 | Neilson | 2/400 |
| 3,608,551 | 7/1971 | Seyo . | |
| 4,605,405 | 8/1986 | Lassen | 604/386 |

*Primary Examiner*—John G. Weiss
*Assistant Examiner*—K. M. Reichle
*Attorney, Agent, or Firm*—Dressler, Goldsmith, Milnamow & Katz, Ltd.

[57] ABSTRACT

An absorbent article embodied as a disposable diaper construction has been particularly configured for improved fit and comfort by providing an absorbent structure attached in a substantially free-floating suspended manner within the diaper. In the illustrated embodiments, the diaper includes an outer cover or back sheet and an absorbent structure or core which is supported within the outer cover by a supporting member which extends along a side of the absorbent structure and includes opposite ends which are secured to the outer cover. The supporting member suspends and supports the absorbent structure for substantially independent movement with respect to the outer cover so that the absorbent structure can conform to the wearer during use thus improving the fit and comfort to the wearer as well as inhibiting leakage from the diaper.

2 Claims, 3 Drawing Sheets

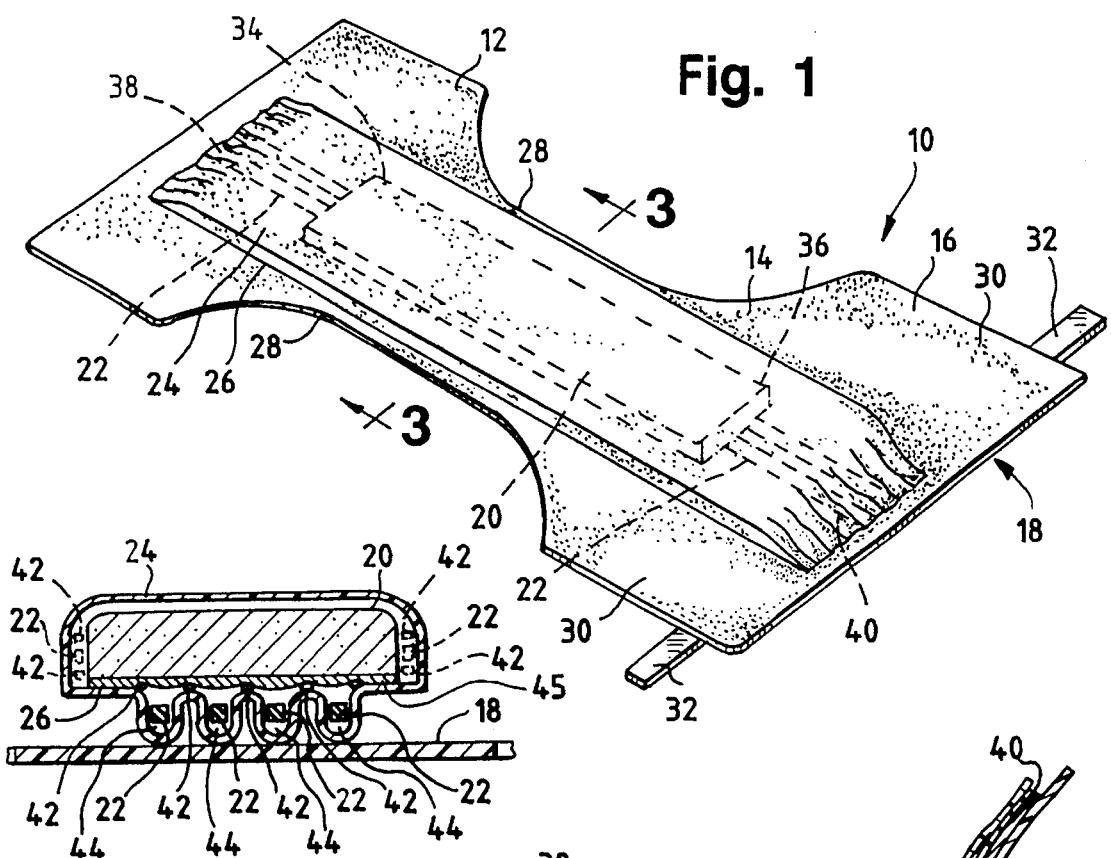
Fig. 1
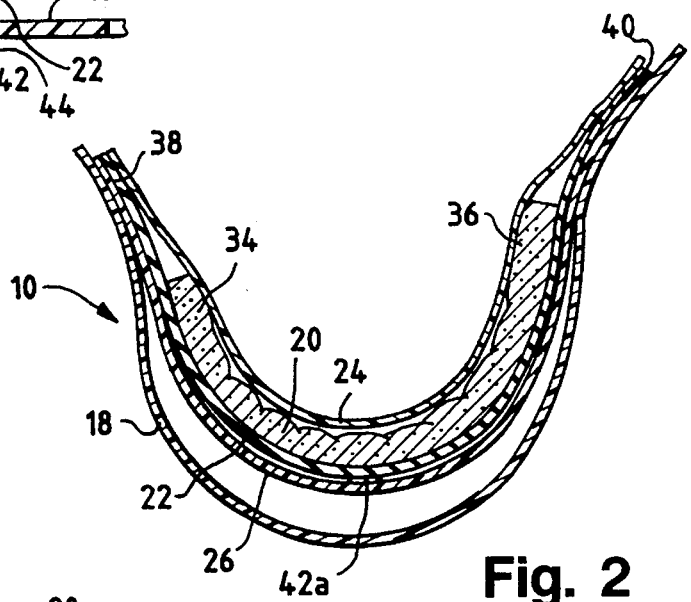
Fig. 2
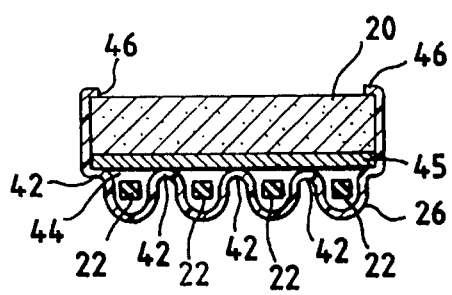
Fig. 3
Fig. 4

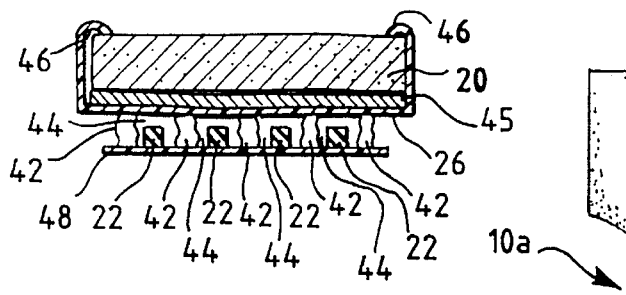
Fig. 5
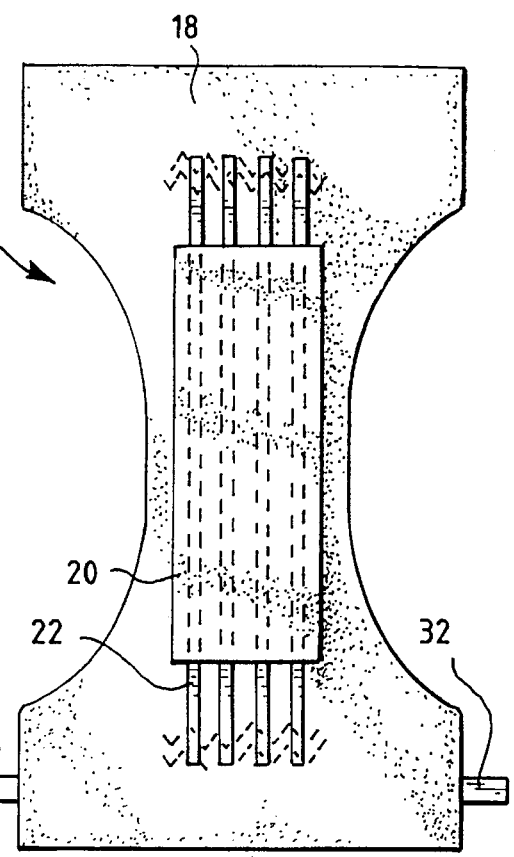
Fig. 6
Fig. 7
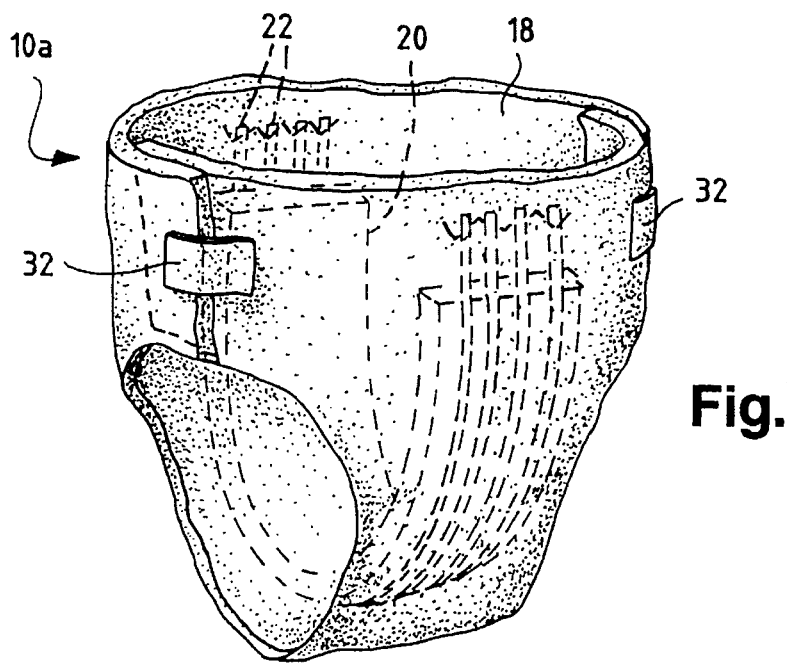
Fig. 8

DISPOSABLE ABSORBENT ARTICLE WITH SUSPENDED ABSORBENT STRUCTURE

TECHNICAL FIELD

The present invention relates generally to disposable absorbent articles such as diapers, training pants or adult incontinent products, and more particularly to a disposable absorbent article having an absorbent structure attached in a substantially free-floating suspended manner therein for improved fit and comfort while exhibiting enhanced absorption and reduced leakage.

BACKGROUND OF THE INVENTION

Disposable absorbent articles, such as infant or adult disposable diapers, generally are categorized into two types, a closed-type article such as a training pant and an open-type article having a flat configuration which includes front, crotch and rear sections. Either article typically includes a liquid impermeable back sheet, a liquid permeable top sheet and an absorbent core interposed therebetween. The core typically is connected along its surface area or at selected portions of its surface area to either the back sheet, the top sheet or both and absorbs and retains waste materials.

One drawback of such conventional integral absorbent articles, however, is that they tend to be displaced away from a wearer's body by movement of the body during use. This displacement causes drooping or sagging of the article in the crotch area and a pronounced bagginess of the article in the front or rear of the article which creates a space between the wearer and the core through which waste materials can leak. As a result, the desired absorbency of the absorbent core can not be fully utilized.

Additionally, leg gathers typically are provided to absorbent articles in the form of one or more elastic elements positioned at the side margins of the diaper. Leg gathers create a gathering force at the side marginal portions of the back sheet and top sheet and generally enhance the fit and comfort of the diaper and reduce leakage through the leg openings. Such leg gathers, however, tend to enhance sagging or bagginess of the inner or medial portion of the diaper since the gathers shorten the side margins while the central or medial portion of the diaper essentially remains at its original length.

Baggy diapers are quite bulky and interfere with the leg movements of the wearer and undesirably expose the typically moisture-impervious backing layer to the inside of the wearer's thighs. Additionally, outer clothing fits very poorly over such a baggy diaper and further adds to the discomfort of the infant or other wearer.

It therefore would be desirable to provide an absorbent article having a substantially free-floating absorbent structure or core suspended from an interior of an outer cover or back sheet for substantially independent movement with respect to the outer cover. Such an article enables the absorbent structure to be held snug against the body of a wearer while allowing the outer cover to move substantially freely with the wearer. This type of absorbent article provides increased absorptive qualities, reduces bagginess and resulting leakage and provides greater freedom of movement to the wearer.

SUMMARY OF THE INVENTION

A disposable diaper or other absorbent article embodying the principles of the present invention has been particularly configured for improved fit and comfort by providing an absorbent structure or core which is suspended within an outer cover or back sheet in a substantially free-floating manner by a supporting member having opposite ends connected to the outer cover. Since the absorbent structure is moveable substantially independently of the outer cover, the absorbent structure can maintain contact with a wearer while the outer cover, which can include leg gathers, is substantially free to move with the wearer.

Accordingly, proper fit and absorbency of the absorbent structure is attained even if the outer cover sags or becomes baggy during use. Furthermore, since the outer cover is somewhat more flexible and less bulky than the absorbent structure, the outer cover readily can be manipulated to enable proper fit of clothing.

In accordance with certain aspects of the invention, the absorbent article may preferably comprise a liquid permeable outer cover or back sheet having a front section and a rear section and an absorbent structure or core having a front end, a rear end and opposite side edges where the front and rear ends are positioned between or within a portion of the front and rear sections of the outer cover.

The supporting member can be in the form of a sheet of extensible or non-extensible material or, preferably, one or more elastic strands or elements. In either event, the supporting member is joined at opposite ends to the outer cover to suspend and support the absorbent structure for substantially independent movement with respect to the outer cover. The supporting member also is joined to the absorbent structure so that it moves substantially independently longitudinally of the absorbent structure and moves substantially independently of the outer cover, except where it is attached to the outer cover.

In the illustrated embodiments, the present disposable diaper is shown as including a generally elongated absorbent structure or core which may comprise any of a large number of different absorbent materials and structures including fiber elements, fibrous matrices and so-called superabsorbent hydrocolloid materials. The absorbent structure preferably is an elongate rectangular member but can be formed in any desired shape.

The absorbent structure preferably includes a substantially fluid impervious barrier layer on at least one side thereof facing the outer cover. The barrier layer prevents liquid not absorbed by the absorbent structure from leaking outside the absorbent structure.

Many different arrangements of the outer cover or back sheet of the present invention may be employed while keeping with the principles discloses herein. The illustrated embodiments include an outer cover formed from a fluid pervious or permeable material, such as a non-woven fabric, to enhance the "breathability" of the diaper.

In the preferred form of the invention, each side margin of the diaper is provided with leg-gathering elastic elements or the like which are positioned generally at the laterally opposite margins of the diaper to conform the diaper to the legs of the wearer. Additionally, to assist in readily removing a training pant from a user without having to pull the diaper down the legs of a user, the side margins of the training pant can be formed with a tear away seam or other design.

As discussed above, leg gathers can sometimes result in bagginess or bulkiness proximate the center of the diaper. The present invention provides a unique attachment of the absorbent structure within the outer cover to conform the absorbent structure to the body of a wearer for improved fit and comfort and to reduce bagginess or bulkiness.

Additionally, the design of the present invention improves the performance of standing leg gathers or internal leg gathers which typically are positioned adjacent to or attached to the absorbent structure. It is believed that standing or internal leg gathers better conform to the body since they are not held back by the outer cover but are allowed to move with the absorbent structure.

Preferably, the invention provides one or more elongate elastic elements which are connected at opposite ends to the outer cover and extend longitudinally beneath an elongate absorbent structure, but can be positioned on the side edges or on top of the absorbent structure if desired. The elongate absorbent structure is not directly attached to any of the elastic elements or to the outer cover in that the elastic elements can lengthen and shorten without corresponding lengthening or shortening of the absorbent structure (i.e., the elastic elements move longitudinally substantially independently of the absorbent structure).

To assist in suspending the absorbent structure and to prevent the elastic element or elements from shifting laterally with respect to the absorbent structure, a sheet of material, such as a non-woven fabric, preferably is utilized to enclose or seal the elastic element with respect to the absorbent structure. The sheet of material creates channels or pockets between the absorbent structure and the sheet of material within which the elastic elements are contained. The channels prevent lateral shifting while permitting longitudinal movement of the elastic elements with respect to the absorbent structure, except at the points of attachment of the elastic elements to the outer cover.

Preferably, the sheet of material essentially provides a backing layer of fluid-pervious or moisture-permeable material, such as a non-woven fabric or the like. This type of fabric enhances the breathability of the diaper structure.

To provide the desired channel or channels, the sheet of material preferably is adhered to the absorbent structure on opposite longitudinal sides of a single elastic member or along the sides and between elastic members if a plurality of elastic members are utilized. The sheet of material can be chosen to substantially correspond to the width of the absorbent structure, wrap around the lateral edges of the absorbent structure or can completely enclose the absorbent structure. When it completely encloses the absorbent structure, the sheet of material provides a liquid-pervious facing layer between the absorbent structure and the wearer as well as a liquid-pervious backing layer. The sheet of material also can be provided with some type of standing or internal leg gather to assist in preventing side leakage about the lateral edges of the absorbent structure.

For the purposes of the present discussions, reference to elastic members or the like is intended to encompass elastic materials, pre-stretched monofilament strands, polyurethane films or foams, elastomeric foams, shrink film and other materials and structures which can be arranged to exert an elastic suspension or gathering force on the associated diaper components. Various arrangements may be employed for securing the elastic member or members to the outer cover and for securing the sheet of material to the absorbent structure to create the above described channels for the elastic members including suitable adhesives, ultrasonic bonding, heat sealing and the like. Examples of elastic elements which can be used with the present invention are disclosed in U.S. Pat. No. 4,935,021 which hereby is incorporated by reference.

In one embodiment, a plurality of elastic members are secured at their ends to the outer cover and are suspended within channels, one each for a respective elastic member, formed by adhering the sheet of material directly to the absorbent structure between the elastic members. Alternatively, a first sheet of material can cover one or more surfaces of the absorbent structure with a second sheet of material secured to selected areas of the first sheet of material to form one or more channels between the two sheets.

In another embodiment, a single elastic element is utilized having a substantial width which approaches the width of the absorbent structure. This wider elastic element preferably is contained within a single channel or layer formed by the sheet of material which is attached to the absorbent structure.

Other features and advantages of the present invention will become readily apparent from the following detailed description, the accompanying drawings and the appended claims.

BRIEF DESCRIPTION OF THE DRAWINGS

FIG. 1 is a perspective view of an absorbent article in the form of a disposable open-type diaper embodying the principles of the present invention;

FIG. 2 is a longitudinal cross-sectional view of the absorbent article of FIG. 1 in a slightly folded position as it typically is utilized illustrating the outer cover, the absorbent structure and the suspension of the absorbent structure from an interior of the outer cover by a supporting member;

FIG. 3 is a lateral cross-sectional view taken along line 3—3 of FIG. 1 in the direction indicated illustrating, in solid lines, one way of attaching one or more elastic members for substantially independent longitudinal movement with respect to the absorbent structure with an alternate attaching method illustrated in dotted lines;

FIG. 4 is a lateral cross-sectional view, similar to FIG. 3, but without the outer cover and illustrating another way of attaching one or more elastic members for substantially independent longitudinal movement with respect to the absorbent structure;

FIG. 5 is a lateral cross-sectional view, similar to FIG. 4; illustrating yet another way of attaching one or more elastic members for substantially independent longitudinal movement with respect to the absorbent structure;

FIG. 6 is a lateral cross-sectional view illustrating a single elastic element of substantial width and its attachment for substantially independent longitudinal movement with respect to the absorbent structure;

FIG. 7 is a top plan view of an absorbent article of the invention without a facing or backing layer about the absorbent structure illustrating attachment of elastic elements directly to the outer cover;

FIG. 8 is a perspective view of the diaper illustrated in FIG. 7 in a folded and secured position as typically utilized by a wearer.

DESCRIPTION OF THE PREFERRED EMBODIMENTS

Figure 9:
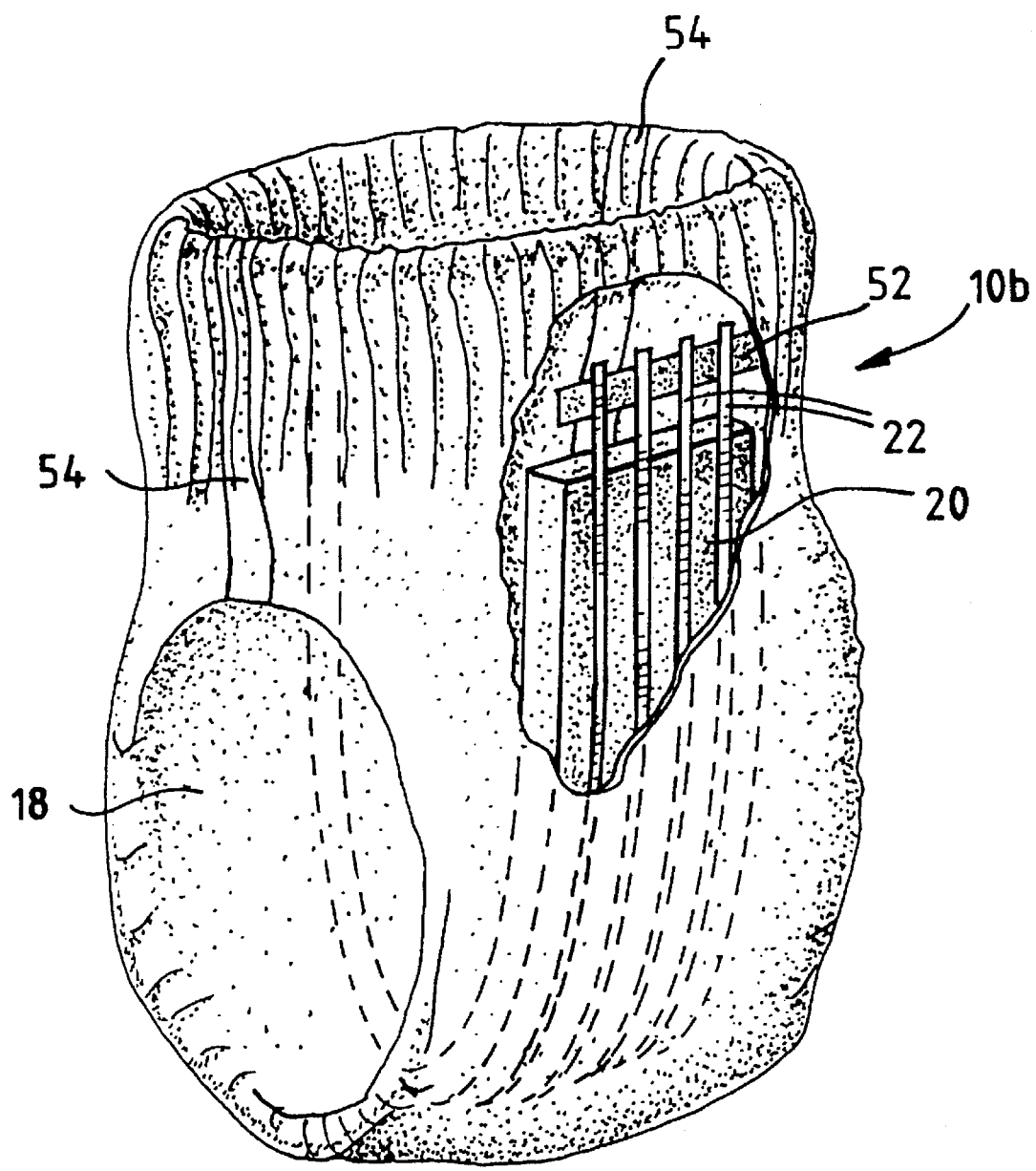
FIG. 9 is a perspective view, partly in section, of a closed-type training pant or pull-up diaper including the suspended absorbent structure of the present invention illustrated without a facing or backing layer and showing direct attachment of the elastic elements to the outer cover.

While the present invention is susceptible of embodiment in various forms, there are shown in the drawings and will hereinafter be described alternate embodiments of the invention, with the understanding that the present disclosure is to be considered as an exemplification of the invention, and is not intended to limit the invention to the specific embodiments illustrated.

Referring to FIGS. 1 and 2, an absorbent article shown as a diaper embodying the principles of the invention is generally designated by the reference numeral 10. As used in the present disclosure, the term diaper is intended to refer to an absorbent article which is worn by an individual for absorbing urine and/or fecal matter. It is to be understood that diapers embodying the principles of the present invention can be appropriately sized for use by infants or babies as well as for use by incontinent adults. Furthermore, absorbent articles embodying the present invention may take the form of sanitary products.

The diaper 10 preferably is disposable and can be an open-type article having a front section 12, a crotch section 14 and a rear section 16. Alternatively, the diaper can be a closed-type article such as a training pant 10b as illustrated in FIG. 9.

As FIGS. 1–3 illustrate, the diaper 10 preferably includes a liquid permeable outer cover or back sheet 18, an absorbent structure or core 20, one or more elongate elastic strands 22, a facing layer 24 and a backing layer 26. To provide the desired fit and reduced bagginess, the absorbent structure 20 is suspended within the confines of the outer cover 18 as described in detail below.

As FIG. 1 illustrates, the outer cover 18 is generally T-shaped or hourglass-shaped having leg cutouts 28 at the laterally opposite margins thereof and a pair of laterally extending ears 30 on the rearward portion of the outer cover 18. If desired, the outer cover 18 can include leg gathers (not illustrated) about the leg cutouts 28. To secure the diaper 10 on a wearer, adhesive tape closures 32 preferably are included with each ear 30 for releasable securement to corresponding tape receiving strips (not illustrated) provided on the forward outside surface of the outer cover 18.

The outer cover 18 can be formed from a substantially moisture-impervious material such as polyethylene or polypropylene; or any elastomeric material. Preferably, the outer cover 18 is formed of a fluid-pervious non-woven or composite material which is relatively hydrophobic. Such a material provides improved breathability for the comfort of the wearer and can be of the type described in detail below with regard to the facing layer 24 and backing layer 26 of the absorbent structure 20.

As FIG. 2 illustrates, the absorbent structure or core 20 substantially is formed as an elongate rectangular member having first and second opposite ends 34 and 36. During use the absorbent structure 20 is suspended within the interior of the outer cover 18 similar to a hammock and is free to move substantially independently with respect to the outer cover 18.

The absorbent structure 20 may comprise any of a variety of well known absorbent structures, including ones having loosely compacted, short cellulosic fibers, such as wood pulp fibers, or cotton linters, or mixtures thereof which primarily are held together by interfiber bonds requiring no added adhesive, as is known in the art. Absorbent structures incorporating so-called superabsorbent hydrocolloid materials also may be employed as well as composite structures employing fibrous material and superabsorbent compounds. Blends of wood pulp fibers and particulate superabsorbent material are particularly suitable.

The absorbent structure 20 preferably is substantially stable and non-extensible. The term "non-extensible", as used herein, refers to an absorbent structure 20 or other member which does not include an elastic element and has an extendibility which is limited to the stretching characteristics of the material or materials from which it is comprised. Such extendibility is limited to approximately 5–10% of the original size of the absorbent structure 20, depending on the material utilized.

Although the absorbent structure 20 is illustrated as being suspended by one or more elastic strands 22, it is to be understood that any type of supporting member can be utilized in place of the elastic strands 22 so long as it functions substantially as described herein. Thus, a sheet of extensible or non-extensible fabric (not illustrated) can be substituted for the elastic strands 22 as well as any other type of material, film, ribbon, netting or the like. Alternatively, the backing layer 26, with or without the facing layer 24, could be substituted for the elastic strands 22.

The elastic strands 22 preferably are elongate having first and second opposite ends 38 and 40 and cooperate to conform the absorbent structure 20 to the wearer's skin. The particular material of the elastic strands 22 can vary, including any type of sheets, films, ribbons, elastic hot-melt adhesives, elastomeric foam and nettings or the like.

As FIGS. 3 and 4 illustrate, preferably four elastic strands 22 are utilized with each absorbent structure 20, but the number can vary depending on the application and the size of the absorbent structure 20. In order to constrain the elastic strands 22 and prevent them from shifting laterally with respect to the absorbent structure 20, the backing layer 26 is secured directly to the absorbent structure 20 between the strands 22, such as with an adhesive 42 or the like. Accordingly, the adhered backing layer 26 forms longitudinal channels 44, one each for a respective elastic strand 22, which span the longitudinal length, or only a portion, of the absorbent structure 20.

As FIG. 3 illustrates, the four elastic strands 22 preferably are positioned along a bottom surface of the absorbent structure 20 between the absorbent structure 20 and the outer cover 18. Alternatively, as illustrated in dotted lines, the elastic strands 22 can be positioned on the side surfaces of the absorbent structure 20 if desired.

It is to be noted that the elastic strands 22 are not substantially attached to the absorbent structure 20 and only are secured to the outer cover 18 at their opposite ends 38 and 40. Accordingly, the elastic strands 22 are constrained against lateral movement yet are free to move substantially independently longitudinally within the channels 44 as desired. This provides the desired support and suspension of the absorbent structure 20 which enables it to adjust to the movements of the wearer and reduce or eliminate any bagginess. Additionally, separate elastic strands 22 provide more freedom of movement of the wearer since they can stretch or contract independent of each other.

As used herein, substantially independent refers to the manner in which the elastic elements 22 can be subjected to significant extension without creating corresponding extension of the absorbent structure 20. In the illustrated embodiment, this substantially independent relationship is provided by indirect securement of the absorbent structure 20 to the elastic elements 22. That is, the one or more elastic elements 22 can move longitudinally within the channels 44 provided by the backing layer 26.

It is further to be contemplated that the preferred substantially independent relationship between the absorbent structure 20 and the elastic elements 22 can be achieved in a variety of ways so long as at least a portion of each elastic element 22 is extensible longitudinally substantially independently of the absorbent structure 20. This relationship can exist even though a portion of the elastic element 22 could be fixedly secured to the absorbent structure 20, such as with adhesive 42a illustrated in FIG. 2 which is shown longitudinally centered with respect to the elastic element 22 and absorbent structure 20 but can vary in position.

The manner in which the elastic strands 22 are secured to the outer cover 18 can vary while keeping with the teachings herein. Various securement techniques can be employed, such as an adhesive, heat or ultrasonic bonding as well as taping.

As FIGS. 1 and 2 illustrate, the elastic strands 22 preferably are provided with their ends 38 and 40 positioned between the facing layer 24 and backing layer 26. The ends 38 and 40 can be secured to either the facing layer 24, the backing layer 26 or both. The facing layer 24 and backing layer 26 with the ends 38 and 40 of the elastic strands 22 therebetween then are secured to the outer cover 18, such as with an adhesive, tape, heat, ultrasonic bonding or the like.

Alternatively, the elastic strands 22 can be longer than the facing layer 24 and backing layer 26 as generally illustrated in FIG. 7 (wherein layers 24 and 26 have been omitted for clarity). In this case, the elastic strands 22 can be secured directly to the outer cover 18 using one or more of the techniques described above or any other method.

The facing layer 24 and backing layer 26 preferably are made from a single sheet of material by surrounding the absorbent structure 20. The material utilized for the facing layer 24 and the backing layer 26 preferably is a moisture pervious material so that the facing layer 24 can be positioned adjacent to the infant or other wearer.

As will be recognized by those familiar with the art, several different types of materials may be used for the fluid-pervious facing layer 24 and backing layer 26. For example, the facing layer 24 and backing layer 26 may be comprised of non-woven webs made of a mixture of fibers consisting predominantly of inexpensive short, cellulosic fibers such as short wood pulp fibers or cotton linters in amounts of 75% to 98%, the balance being textile length fibers such as rayon, as known in the art.

Preferably, the facing layer 24 and backing layer 26 are made from a hydrophobic non-woven fabric, with the facing layer treated with a surfactant to encourage liquid migration into the absorbent structure 20. The preferred use of hydrophobic fabric for layers 24 and 26 discourages leakage out of the absorbent structure 20.

Alternatively, the facing layer 24 and backing layer 26 can be formed from an apertured non-woven or other fabric made of naturally occurring fibers, synthetic fibers, or blends thereof. For example, the fabric may be polyester, polyethylene, polypropylene, nylon, rayon or the like.

In addition, the facing layer 24 and backing layer 26 may be made from non-apertured materials such as non-woven isotropic webs or apertured polyolefin or polyester films having the desired moisture permeability. Spun-bonded and melt-blown fabrics can also be employed.

Accordingly, a variety of different materials may be employed for the fluid-pervious layers 24 and 26 so long as they are relatively hydrophobic so as to retard wicking. Additionally, it is preferable that the material of the layers 24 and 26 is of the type which, after permeation by moisture, prevents strike-back of body fluid when the absorbent structure 20 is approaching saturation.

It is to be noted that, if desired, the facing layer 24 and/or backing layer 26 can include leg gathers (not illustrated).

Thus, such leg gathers would be positioned directly adjacent the side edges or surfaces of the absorbent structure 20 and would better conform to the body since they would be allowed to move with the absorbent structure 20 and would not be held back by the outer cover 18.

As FIG. 3 illustrates, in order to prevent leakage of liquid from the absorbent structure 20 through the backing layer 26 and outer cover 18, a substantially moisture-impervious barrier layer 45 is positioned between the elastic strands 22 and the absorbent structure 20 and is secured to the absorbent structure 20 with an adhesive or the like. The backing layer 26 preferably is adhered directly to the barrier layer 45 or can be adhered directly to the absorbent structure 20 if no barrier layer 45 is included.

The barrier layer 45 may be formed from a separate sheet of flexible moisture-impervious material such as polyethylene or polyethylene terephthalate. Alternatively, a coating of a liquid-impervious material, such as hot-melt adhesives or hydrophobic coatings of silicone or fluorocarbon compounds can be applied to the bottom of the absorbent structure 20 to provide the desired barrier properties. It also is possible to employ liquid-impervious, vapor-pervious fabrics and films for use as the outer cover or outer layer 18 instead of or in addition to a barrier layer 45.

FIGS. 4, 5 and 6 illustrate alternate embodiments of the facing layer 24 and backing layer 26. Elements in these embodiments which are substantially the same as in the embodiment of FIGS. 1–3 are so-designated by like reference numerals.

FIG. 4 illustrates another embodiment of the invention which substantially does not include a facing layer 24. Top edges 46 of the backing layer 26 are secured to a top or side surface of the absorbent structure 20 with an adhesive or the like.

FIG. 5 illustrates another embodiment of the invention which does not include a facing layer 24 and where the backing layer 26 is not adhered to the absorbent structure 20 between the elastic strands 22 to form the channels 44. In this embodiment, a second backing layer or sheet 48 is provided which is secured to the backing layer 26 between the elastic strands 22 with adhesive 42 to provide the channels 44 and capture the elastic strands 22 between the backing layer 26 and the second backing layer 48.

FIG. 6 illustrates yet another embodiment of the invention which does not include a facing layer 24 and where the elastic strands 22 are replaced with a single, much wider elastic member 50. To provide a channel 44a for the elastic member 50, edges 46a of the backing layer 26 are secured to the barrier layer 45 or absorbent structure 20 on either side of the elastic member 50 with adhesive 42. It is to be understood that the width, thickness and material of the elastic member 50 can vary.

FIGS. 7 and 8 illustrate another embodiment of the diaper 10a of the present invention, substantially similar to the diaper 10 of FIG. 1, where the facing and backing layers 24 and 26 are removed for clarity. In this embodiment, the elastic strands 22 would extend beyond the opposite ends of the facing and backing layers 24 and 26 and are directly attached to the outer cover 18 with an adhesive, such as spray hot melt adhesive, by heat-bonding, such as ultrasonic bonding, or with adhesive tape.

Although the facing layer 24 and backing layer 26 are not illustrated in this embodiment, any of the arrangements of the facing and backing layers 24 and 26 illustrated in FIGS. 3–6 can be utilized so long as the elastic strands 22 or members 50 are Secured directly to the outer cover 18.

FIG. 9 generally illustrates a closed-type diaper 10b in the form of a training pant or pull up including an absorbent structure 20 and elastic strands 22 but without the facing and backing layers 24 and 26. The diaper 10b can include any of the arrangements of the facing layer 24 and backing layer 26 of the embodiments of FIGS. 3–8. FIG. 9 also illustrates elastic strands 22 which would extend beyond the ends of the facing layer 24 and backing layer 26 and are directly secured to the outer cover 18 with one or more pieces of tape 52 or any other method as described above.

To easily remove the diaper 10b, two tearable side seams 54 preferably are provided on opposite lateral sides of the diaper 10b. The side seams 54 can be provided by an adhesive, by ultrasonic bonding or in any other desired way so long as easy removal of the diaper 10b is provided.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. An absorbent article, comprising:

a liquid permeable outer cover having a front section and a rear section;

a substantially non-extensible elongate absorbent structure having a front end, a rear end, top and bottom surfaces and opposite side surfaces, said absorbent structure being positioned within said outer cover with said front and rear ends of said absorbent structure extending into said front and rear sections of said outer cover, respectively, said absorbent structure including a barrier layer on at least one surface thereof facing said outer cover;

at least one elastic element having opposite ends joined to said front and rear sections of said outer cover, respectively, for suspending and supporting said absorbent structure for substantially independent movement with respect to said outer cover and for enabling substantially independent longitudinal movement of said at least one elastic element with respect to said absorbent structure and said outer cover except at said opposite joined ends so that said absorbent structure can conform to a body of a wearer during use; and a channel positioned on one surface of said absorbent structure and extending between said front and rear ends thereof, said at least one elastic element being positioned within said channel for laterally constraining said at least one elastic element with respect to said absorbent structure and enabling said substantially independent longitudinal movement of said at least one elastic element with respect to said absorbent structure and said outer cover and enabling said absorbent structure to conform to the body of the wearer during use, wherein said channel is formed by a sheet of liquid permeable material and including means for attaching said sheet with respect to said absorbent structure for enabling said substantially independent longitudinal movement of said at least one elastic element, wherein said sheet completely surrounds said absorbent structure and said at least one elastic element, and includes first and second opposite longitudinal ends connected to said front and rear sections, respectively, of said outer cover.

2. An absorbent article in accordance with claim 1 wherein said at least one elastic element includes a plurality of elastic elements and said sheet is secured to said absorbent structure between each elastic element to provide a plurality of channels, one each for a respective elastic element.

\* \* \* \* \*